US005789654A

United States Patent [19]
Lowell et al.

[11] Patent Number: 5,789,654
[45] Date of Patent: Aug. 4, 1998

[54] TRANSGENIC ANIMALS DEFICIENT IN ENDOGENOUS $\beta_3$-ADRENERGIC RECEPTOR AND USES THEREOF

[75] Inventors: Bradford B. Lowell, Southborough, Mass.; A. Donny Strosberg, Paris, France

[73] Assignees: Beth Israel Hospital Association, Boston, Mass.; Centre National de la Recherche Scientifique, Paris, France

[21] Appl. No.: 647,118

[22] Filed: May 9, 1996

[51] Int. Cl.⁶ .............................. C12N 5/00; C12N 15/00; C12N 15/09
[52] U.S. Cl. ..................... 800/2; 435/172.3; 435/69.1; 435/320.1; 435/6; 435/325; 424/9.2
[58] Field of Search ..................... 800/2; 435/172.3, 435/69.1, 320.1, 6, 240.2, 325; 424/9.2

[56] References Cited

U.S. PATENT DOCUMENTS 5,288,607  2/1994  Emorine et al. .............................. 435/6

OTHER PUBLICATIONS

Susulic et al., Journal of Cellular Biochemistry, Suppl. 18A, p. 172, 1994.
Bradley et al., Biotechnology, vol. 10, pp. 534–539, 1992.
Emorine et al., "Molecular Characterization of the Human $\beta_3$-Adrenergic Receptor", Science, 345:1118–1121.
Lowell et al., Nature 366:740–742, 1993.
Maffei et al., Proc. Natl. Acad. Sci. USA 92:6957–6960, 1995.
Revelli et al., Experientia 51.A30, 1995.
Susulic et al., Journal of Biological Chemistry 270:29483–29492, 1995.
Susulic et al., The Endocrine Society 77th Annual Meeting, Session S35 p. 36, 1996.

*Primary Examiner*—Jasemine C. Chambers
*Assistant Examiner*—Jill D. Schmuck
*Attorney, Agent, or Firm*—Clark & Elbing LLP

[57] ABSTRACT

Disclosed a transgenic non-human mammal whose germ cells and somatic cells contain a knockout mutation in DNA encoding $\beta_3$-adrenergic receptor polypeptide.

13 Claims, 10 Drawing Sheets

| Enzyme | Probe | Wild-type Allele | Recombinant Allele |
|---|---|---|---|
| Pst-I | A | 11 kb | 7 kb |
| Pst-I | B | 11 kb | 7 kb |
| Hind-III | C | 10 kb | 8 kb |

# 5,789,654

TRANSGENIC ANIMALS DEFICIENT IN ENDOGENOUS $\beta_3$-ADRENERGIC RECEPTOR AND USES THEREOF

STATEMENT AS TO FEDERALLY SPONSORED RESEARCH

This invention was made in part with Government funding, and the Government therefore has certain rights in invention.

BACKGROUND OF THE INVENTION

This invention relates to transgenic animals lacking the endogenous $\beta_3$-adrenergic receptor.

Obesity is a prevalent disorder that often leads to diabetes, cardiovascular disease, and joint disorders. The development of obesity is thought to represent the dysregulation of various homeostatic mechanisms that normally function to maintain normal body weight. Recent studies using transgenic mice with induced brown fat deficiency (Lowell et al., Nature 366:740–742, 1993) have indicated that this tissue is important for regulating energy balance in mice, and that brown adipose tissue dysfunction can cause obesity and diabetes.

The activity of brown adipose tissue is controlled by the sympathetic nervous system (Himms-Hagen, Prog. Lipid Res. 28:67–115, 1989). Locally released norepinephrine stimulates brown adipocytes via adrenergic receptors (ARs). Available evidence indicates that $\beta$-ARs, rather than $\alpha$-ARs, mediate norepinephrine induced thermogenesis in brown fat (Bukowiecki, Can J Biochem. Cell Biol. 62:623–630, 1984). Brown and white adiopcytes are known to express $\beta_1$-, $\beta_2$-, and $\beta_3$-ARs, with $\beta_3$-AR being the most abundant subtype in rodents (Collins et al., Mol. Endocrinology 8:518–527, 1994). The genes encoding the human (Emorine et al., Science 245:1118–1121, 1989), rat (Granneman et al., Mol. Pharm. 44:264–270, 1991; Muzzin et al., J. Biol. Chem. 266:24053–24058, 1991), and mouse (Nahmias et al., EMBO J. 10:3721–3727, 1991) $\beta_3$-AR have been cloned, and their amino acid sequences are 40–50% homologous to that of the $\beta_1$- and $\beta_2$-ARs. Expression of $\beta_3$-AR is reduced in genetically obese rodents, leading to the speculation that this gene may contribute to the development of obesity (Muzzin et al., J. Biol. Chem. 266:24053–24058, 1991; Collins et al., Mol. Endocrinology 8:518–527, 1994).

A number of selective agonists have been synthesized for $\beta_3$-AR, and administration of such compounds to rodents has been found to increase energy expenditure by more than two-fold (Cawthorne et al., Am. J. Clin. Nutr. 55:252S–257S, 1992; Holloway et al., Am. J. Clin. Nutr. 55:262S–264S, 1992; Bloom et al., J. Med. Chem. 35:3081–3084, 1992). Furthermore, when these compounds are chronically administered to genetically obese rodents, obesity and insulin resistance were found to be improved (Cawthorne et al., supra; Holloway et al., supra.; Bloom et al., supra). Given the usefulness of $\beta_3$-AR agonists in stimulating AR activity, it is desirable to develop a transgenic animal system that is useful for detecting and determining the pharmacological properties of such compounds.

SUMMARY OF THE INVENTION

In general, the invention features a transgenic non-human mammal whose germ cells and somatic cells contain a knockout mutation in DNA encoding an endogenous $\beta_3$-adrenergic receptor polypeptide. In preferred embodiments, the transgenic mammal also includes germ cells and somatic cells expressing DNA encoding a human $\beta_3$-adrenergic receptor polypeptide (e.g., in brown adipose tissue).

In another aspect, the invention features a method of producing a transgenic non-human mammal capable of expressing a functionally active human $\beta_3$-adrenergic receptor polypeptide, the non-human mammal lacking expression of the endogenous $\beta_3$-adrenergic receptor polypeptide, the method includes: (a) providing a transgenic non-human mammal whose germ cells and somatic cells contain a knockout mutation in DNA encoding $\beta_3$-adrenergic receptor polypeptide; (b) introducing a human $\beta_3$-adrenergic transgene derived from a human $\beta_3$-adrenergic polypeptide gene into a cell of the non-human mammal, the transgene being capable of expressing a human $\beta_3$-adrenergic receptor polypeptide; and (c) obtaining progeny containing of the non-human mammal containing the transgene. In preferred embodiments, the human $\beta_3$-adrenergic transgene is expressed in brown adipose tissue.

In other related aspects, the invention features a cell line isolated from a transgenic non-human mammal according to the invention.

In another aspect, the invention features a method of screening for a compound that increases human $\beta_3$-adrenergic receptor activity, the method including: exposing the non-human transgenic mammal of the invention to the compound, and determining the activity of the human $\beta_3$-adrenergic receptor in the mammal, an increase in the receptor activity as compared to untreated non-human mammals being indicative of a compound being capable of increasing human $\beta_3$-adrenergic receptor activity. In preferred embodiments, the method includes determining oxygen consumption; energy expenditure; food intake; insulin secretion; glycemic control; lipolysis using brown fat adipocytes; and adenylate cyclase activity using brown fat adipocytes.

By "transgenic" is meant any mammal which includes a nucleic acid sequence which is inserted by artifice into a cell and becomes a part of the genome of the animal that develops from that cell. Such a transgene may be partly or entirely heterologous to the transgenic animal. Although transgenic mice represent a preferred embodiment of the invention, other transgenic mammals including, without limitation, transgenic rodents (for example, hamsters, guinea pigs, rabbits, and rats), and transgenic pigs, cattle, sheep, and goats may be constructed by standard techniques and are included in the invention.

By "knockout mutation" is meant an alteration in the nucleic acid sequence that reduces the biological activity of the polypeptide normally encoded therefrom by at least 80% relative to the unmutated gene. The mutation may, without limitation, be an insertion, deletion, frameshift mutation, or a missense mutation. Preferably, the mutation is an insertion or deletion (e.g., the PGK-NEO knockout gene described herein), or is a frameshift mutation that creates a stop codon.

By "regulatory region" is meant a sequence which is minimally necessary for directing transcription and, if appropriate, translation of an associated nucleic acid coding sequence. The term may also include auxiliary sequences that mediate gene expression in response to an external or internal stimulus, for example, expression that is inducible (for example, by temperature or a chemical stimulus) or expression that is tissue-specific (for example, nervous system-specific) or developmental stage-specific. "Regulatory region" sequences are generally located 5' (or "upstream") of the nucleic acid coding sequence, but may be located within or 3' (or "downstream") of the coding sequence.

As described herein, the invention provides a number of advantages. Because transgenic animals are generally useful for the investigation of specific biological processes and for reproducing particular aspects of human disease and metabolism, the transgenic animals of the invention provide an important and accurate means for screening drugs to isolate therapeutic agents. In particular, the transgenic animals expressing human $\beta_3$-adrenergic receptor described for the first time herein have the advantage of preferentially expressing human $\beta_3$-adrenergic receptor in particular fat tissues (e.g., brown fat or white fat), preferably in the absence of expression of the endogenous $\beta_3$-AR gene (e.g., the mouse $\beta_3$-AR gene). Because this invention provides a transgenic non-human mammal model of human $\beta$-adrenergic receptor expression, compounds may be screened to identify those which stimulate $\beta_3$-AR synthesis or activity. Such stimulants have use as anti-obesity and anti-diabetes agents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In addition, the materials, methods, and examples described in this specification are illustrative only, and not intended to be limiting.

Other features and advantages of the invention will be apparent from the following detailed description, and from the claims.

DETAILED DESCRIPTION

The drawings will first be described.

DRAWINGS

FIGS. 1A–B are schematic illustrations showing the $\beta_3$-AR gene, targeting vectors, and Southern blot detection schemes.

FIG. 1A is an illustration showing a partial restriction enzyme map of the $\beta_3$-AR gene, the $\beta_3$-AR-knockout mutation, $\beta_3$-KO, (mouse zygote) and $\beta_3$-KO+TK (ES cell) targeting vectors, and the predicted structure of the recombinant allele. The targeting vectors contain 12 kb of homologous $\beta_3$-AR genomic DNA, with 5 kb located 5' and 7 kb located 3' of the PGK-NEO-Poly(A) cassette (Adra et al., *Gene* 60:65–74, 1987). The PGK-NEO-Poly(A) vector replaces 306 bp of $\beta_3$-AR coding sequence between NheI and XhoI corresponding to $\beta_3$-AR residue 120, in the middle of the third transmembrane domain, to residue 222, at the COOH-terminal end of the fifth transmembrane domain. In addition, the $\beta_3$-KO+TK targeting vector contains the HSV-TK expression cassette, pIC19R/MC1-TK (Mansour et al., *Nature* 336:348–352, 1988), as well as plasmid sequence on the 3' end. Southern blot probes A and C are located outside of the targeting vector sequence. Boxes refer to exons, the locations of which have been described by Van Spronsen et al. (*Eur. J. Biochem.* 213:1117–1124, 1993) and Granneman et al. (*Mol. Pharmacol.* 42:964–970, 1992). The translated segments are shown in black. Arrows refers to orientation of transcription. Restriction enzyme sites are denoted as follows: B, BamHI; H, HindIII; K, KpnI; N, NheI; P, PstI; S, SalI; X, XhoI.

FIG. 1B is a description of the probes used for Southern analysis.

FIGS. 2A–B are photographs showing the Southern blot analysis of ES cell and mouse tail genomic DNA. Genomic DNA was digested with PstI, electrophoresed, blotted, and then hybridized to probe A (as shown in FIG. 1B).

FIG. 2A shows the Southern analysis of ES cell clone DNA. Three G418-resistant ES cell clones are shown. Clones 2 and 3 have targeted disruption of the $\beta_3$-AR gene.

FIG. 2B shows the Southern analysis of mouse tail DNA. Two mice known to be wild type (+/+), two knockout founders (B1-F and B2-F), two heterozygous offspring of the founders (B1-30 and B2-5), and two homozygous knockout offspring of a cross between B1-30 and B2-F (B1.2 (−/−)) are shown.

FIG. 3 is a photograph of a $\beta_3$-AR RNase protection assay. $\beta_3$-AR and actin mRNA levels were determined in brown adipose tissue and liver samples using an RNase protection assay. Samples were obtained from the offspring of a cross between two heterozygous mice. Genotype was determined by Southern blotting.

FIG. 4 is a panel of photographs showing $\beta_1$-, $\beta_2$-, and $\beta_3$-AR mRNA levels in white and brown adipose tissue by Northern blotting. $\beta_1$-, $\beta_2$-, and $\beta_3$-AR mRNA levels were determined by Northern blotting using thirty micrograms of total RNA isolated from epididymal white adipose tissue and interscapular brown adipose tissue of five control (C) and five $\beta_3$-AR-deficient (K) twelve-week-old male mice. Representative lanes from two control and two $\beta_3$-AR-deficient samples are shown. PhosphorImager analyses of Northern blots were performed using all five control and five $\beta_3$-AR-deficient samples. The blots were also hybridized with a $\beta$-actin probe. The approximate sizes (in kb) of the detected signals are as follows: $\beta_1$-AR, ~2.4; $\beta_2$-AR, ~2.4; $\beta_3$-AR, ~2.4; and $\beta$-actin, ~2.1.

FIGS. 5A–B are graphs showing the results of adenylate cyclase activity in response to CL 316,243 and isoproterenol. Membranes were obtained from isolated white adipocytes and brown adipose tissue of eight twelve-week-old male wild type (+/+) and $\beta_3$-AR-deficient (−/−) littermates, and then assayed for adenylate cyclase activity.

Figure 6A:
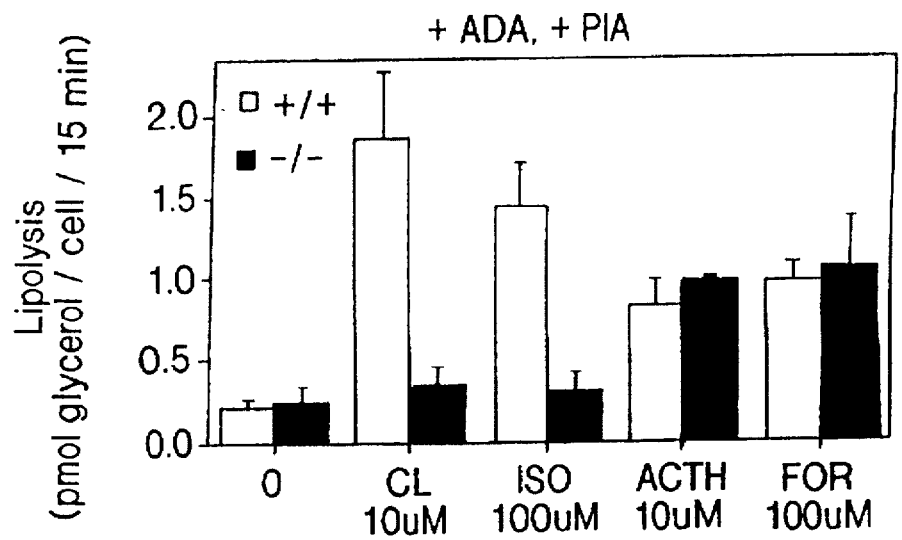
Figure 6B:
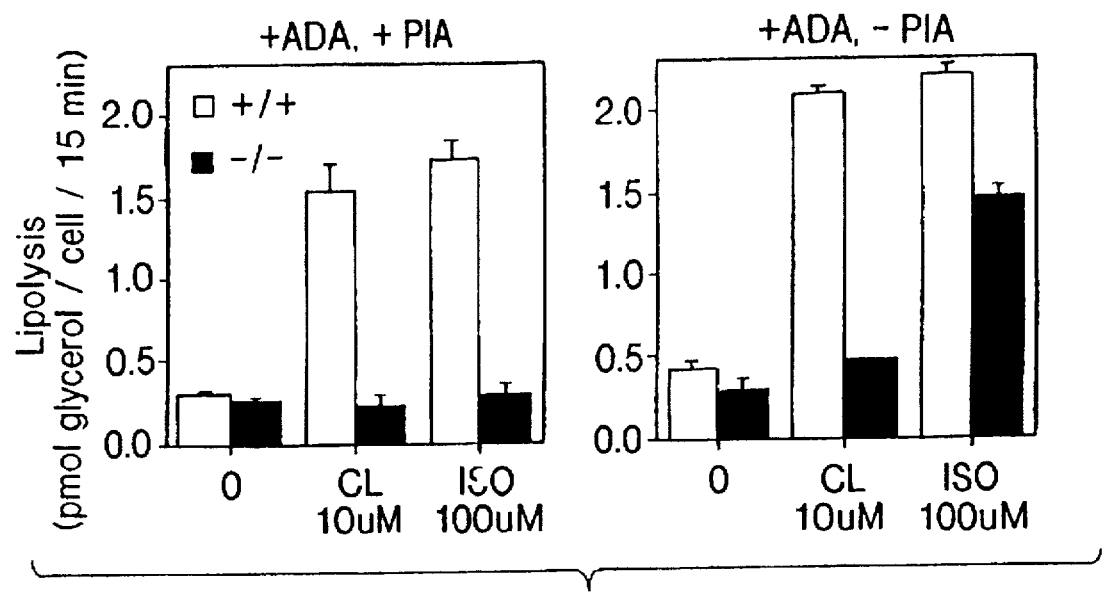

FIGS. 6A–B are graphs showing lipolysis in isolated white adipocytes. White adipocytes were isolated from epididymal fat pads of eight twelve-week-old male wild type (+/+) and $\beta_3$-AR-deficient (−/−) littermates, and then assayed for glycerol release as an indicator of lipolysis.

FIG. 6A is a graph showing the results of several lipolysis assays that were performed in the presence of adenosine deaminase (ADA) and PIA ($N^6$-[R-(−)-1-methyl-2-phenyl] adenosine). Average fat cell sizes (ng of lipid/cell) were 216±14 for control cells and 248±22 for knockout cells. Results are expressed as the mean (±S.E.) of ten experiments.

FIG. 6B are graphs showing the results of lipolysis assays that were performed in the presence of adenosine deaminase, with or without PIA. Average fat cell sizes (ng of lipid/cell) were 203±18 for control cells and 167±10 for knockout cells. Both FIGS. 6A and 6B represent results of assays performed on the same day (with or without PIA) and are the mean (±S.E.) of three experiments.

Figure 7:
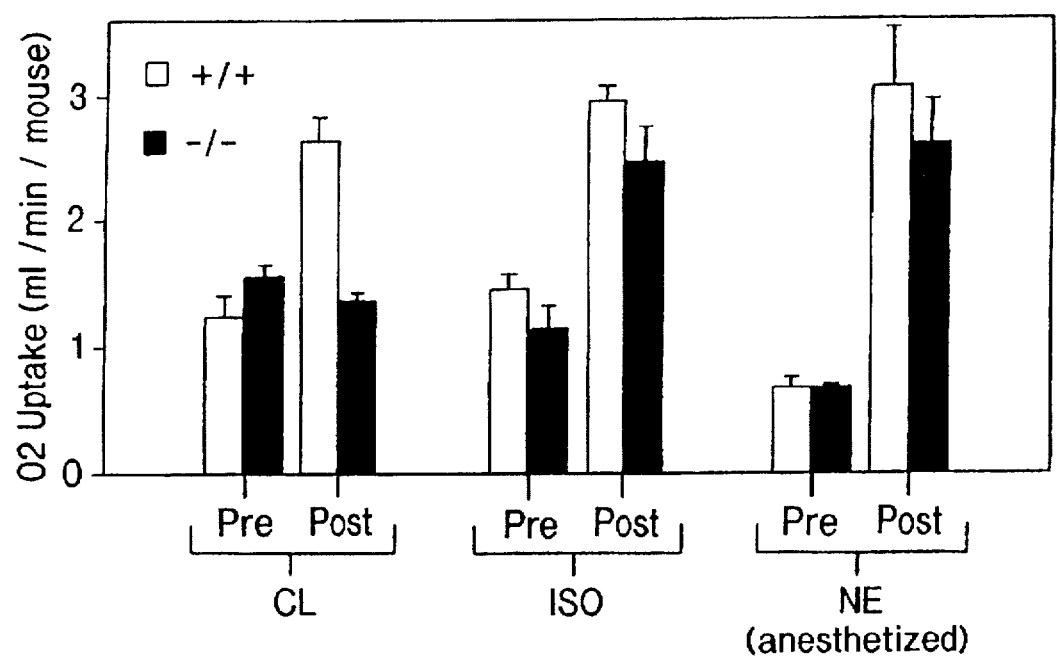

FIG. 7 is a graph showing the effects of CL 316,243, isoproterenol, and norepinephrine on $O_2$ consumption. Control (+/+) and $\beta_3$-AR-deficient (-/-) male mice, ten to twelve weeks old, were treated with either CL 316,243 (1.0 mg/kg, subcutaneously), isoproterenol (ISO, 0.3 mg/kg, subcutaneously), or norepinephrine (NE, 0.6 mg/kg subcutaneously), and effects on $O_2$ consumption were assessed. Mice that received CL 316,243 and isoproterenol were awake and unrestrained for the study. Mice that received norepinephrine were anesthetized with pentobarbital for the study. The results are expressed as the mean ±S.E. (CL, +/+=six mice, -/-=five mice; isoproterenol, +/+=four mice, -/-=four mice; norepinephrine, +/+=four mice, -/-=three mice).

Figure 8A:
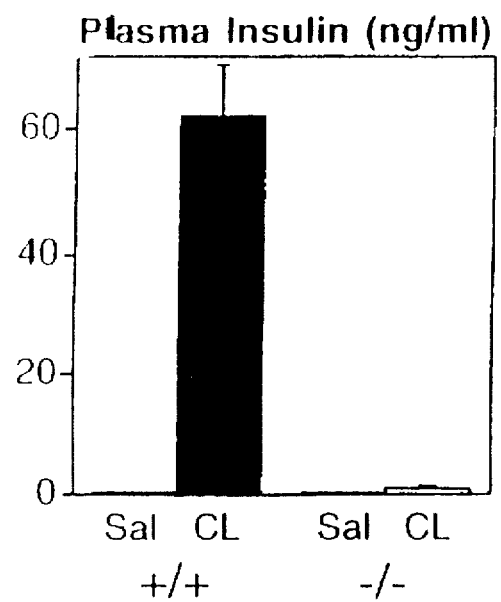
Figure 8B:
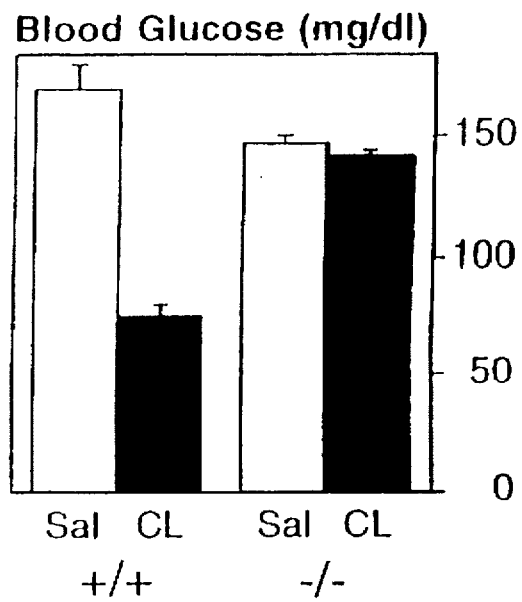

FIGS. 8A-B are graphs showing the acute effect of saline or CL 316,243 on plasma insulin and blood glucose concentrations. Wild type (+/+) and $\beta_3$-AR-deficient (-/-) female littermates (eight weeks old) were treated with an intraperitoneal injection of either saline (Sal) or CL 316,243 (1 mg/kg). Blood was obtained from the tail fifteen minutes after infection. The results are expressed as the mean ±S.E. (+/+=seven mice, -/-=four mice).

FIG. 8A is a graph showing the acute effect of saline or CL 316,243 on plasma insulin.

FIG. 8B is a graph showing the acute effect of saline or CL 316,243 on blood glucose concentrations.

Figure 9:
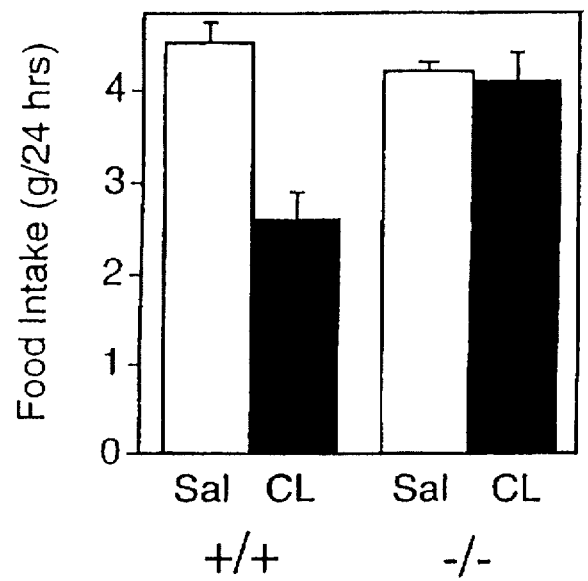

FIG. 9 is a graph showing the effect of a single dose of CL 316,243 on food intake. Wild type (+/+) and $\beta_3$-AR-deficient (-/-) male littermates (8 weeks old) were treated with an intraperitoneal injection of either saline (SAL) or CL 316,243 (1 mg/kg). The mice were housed individually during the test period, and results for each group are the mean of five animals (±S.E.). Food intake was determined during the twenty-four hours following CL 316,243 or saline treatment.

Figure 10:
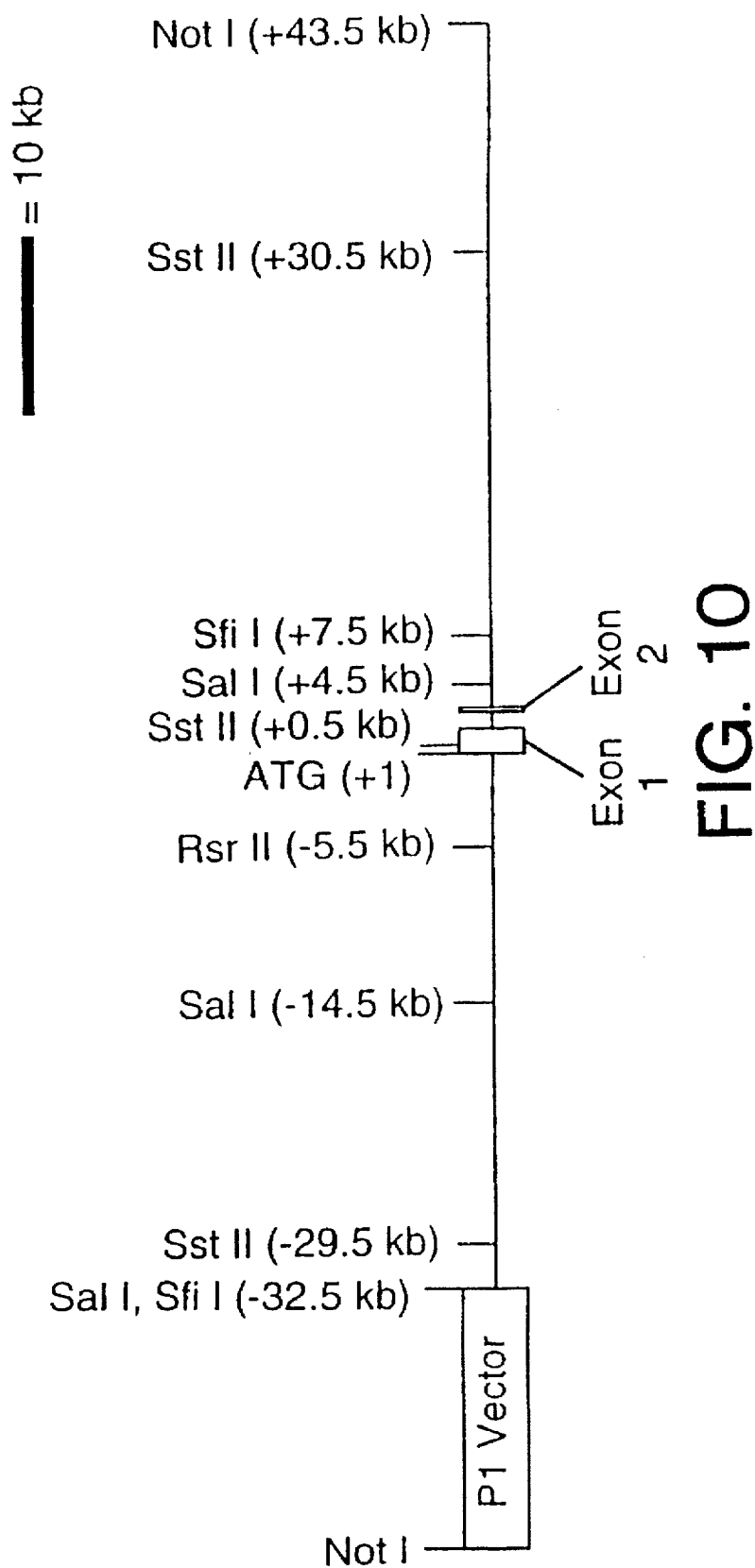

FIG. 10 is a schematic illustration of the human $\beta_3$-AR receptor gene in the P1 vector.

Figure 11:
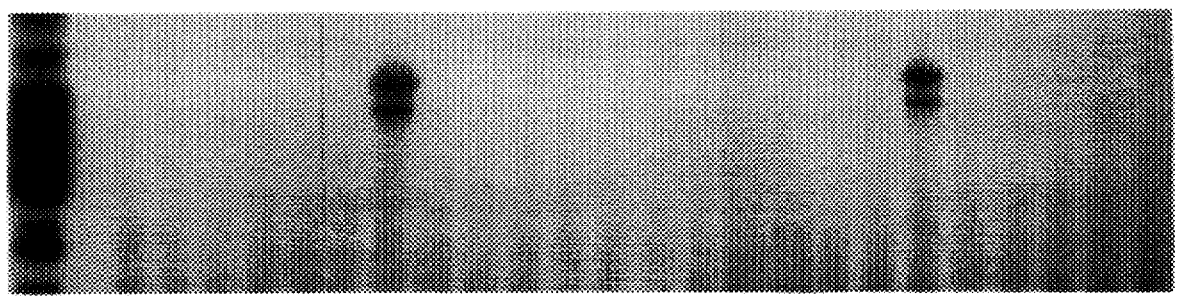

FIG. 11 is a photograph of an RNAse protection assay showing the expression of the human $\beta_3$-AR gene in various tissues of $\beta_3$-AR deficient (-/-) mice.

Figure 12:
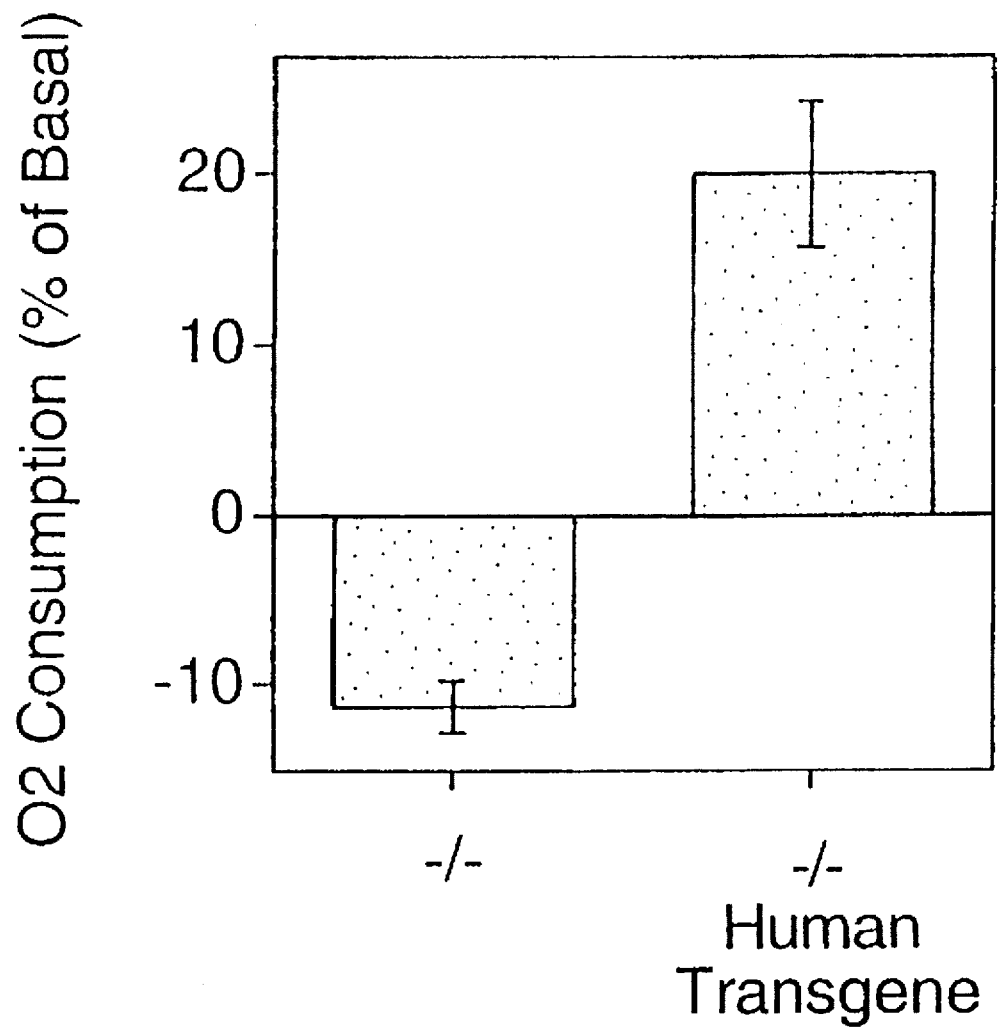

FIG. 12 is a graph showing the effect of CGP-12177 (10 mg/ml) on $O_2$ consumption in $\beta_3$-AR deficient (-/-) transgenic mice and $\beta_3$-AR deficient (-/-) transgenic mice expressing the human $\beta_3$-AR gene.

The transgenic animals of the invention are described in detail below. In general, these animals are produced by creating a construct that knocks out the expression of endogenous $\beta_3$-AR gene (e.g., the murine $\beta_3$-AR gene). This construct is amplified in bacterial cells, purified, and injected into isolated oocytes or ES cells. For example, transformed oocytes are then implanted into pseudopregnant females, and the resulting knockout offspring that have incorporated the foreign gene into their genomes are identified. From these founder mice, several distinct animal lines are produced by breeding with wild-type animals. The heterozygotes produced are then bred together to obtain homozygotes possessing the disrupted allele on both chromosomes. These homozygotes may be bred indefinitely and are used in a series of experiments (e.g., those described herein) to characterize the transgenic mouse phenotype. $\beta_3$-AR deficient animals are used for reconstituting the expression of $\beta_3$-AR using the human gene and its accompanying regulatory elements, including a promoter that directs the preferential expression of human $\beta_3$-AR gene in brown adipose tissue (e.g., using the UCP promoter described by Lowell et al., Nature 366:740-742 or the endogenous human $\beta_3$-AR promoter as described herein). Alternately, human $\beta_3$-AR gene is expressed in white and brown adipose tissue, e.g., by using the aP2 promoter.

The transgenic animals described herein exhibit impairments in $\beta_3$-AR activity. In addition, $\beta_3$-AR deficient transgenic animals expressing human $\beta_3$-AR gene in brown fat were also generated.

Targeting in ES Cells

Figures 1A, 1B:
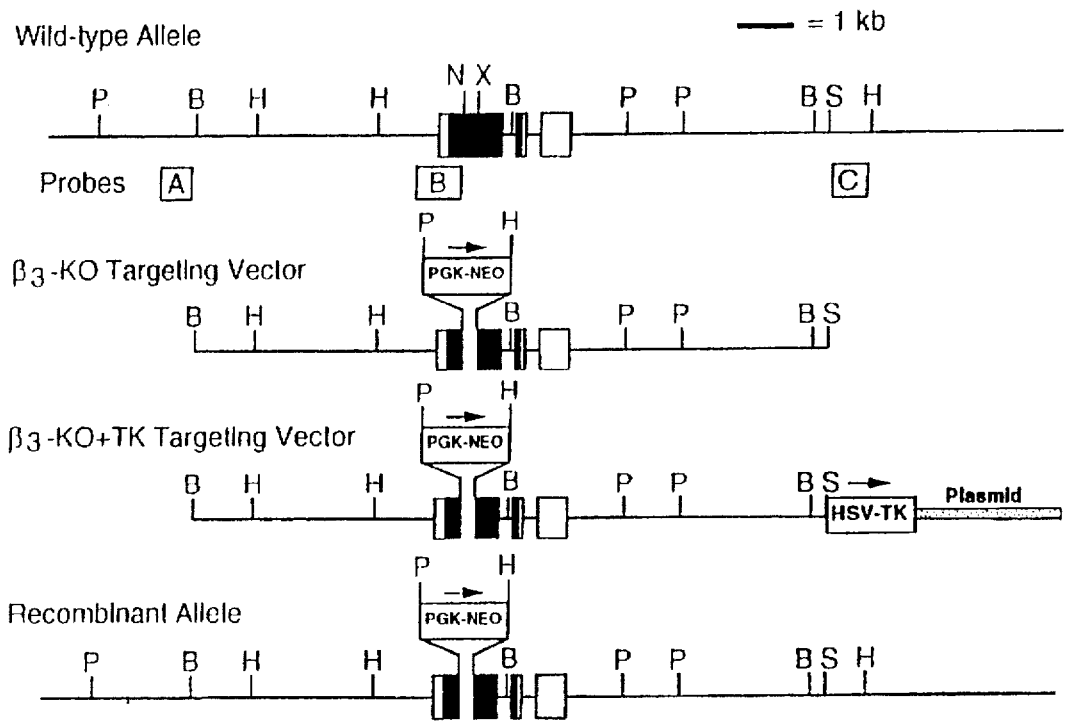
Figure 2A:
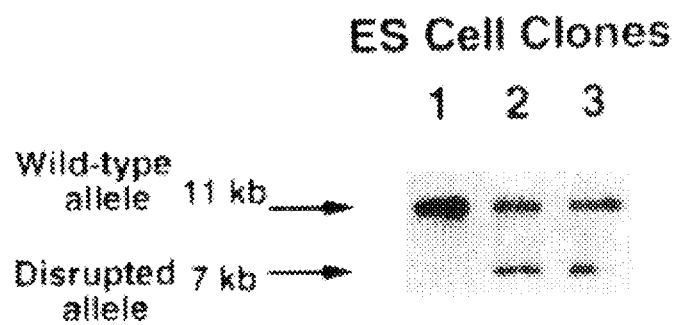

The $\beta_3$-KO+TK construct (FIG. 1) was electroporated into J1-ES cells and drug-resistant clones were selected. Genomic DNA was isolated and subjected to Southern blot analysis (FIGS. 1 and 2A). Approximately fifty percent of the G418-resistant clones and seventy-five percent of the G418, FIAU (1-[2-deoxy, 2-fluoro-β-D-arabinofuranosyl]-5-iodouracil) doubly resistant clones had targeted disruption of the endogenous $\beta_3$-AR gene, indicating that homologous recombination events occurred at a frequency that equaled random integration events. The results of two independent ES cell transfections are shown in Table I (below). In experiment 1, transfected cells were divided and treated with either positive selection alone (G418) or both positive and negative selection (G418 and FIAU). In experiment 2, transfected cells were treated with G418 alone.

TABLE I

| Selection | No. of colonies analyzed | No. of homologous recombination events |
|---|---|---|
| Experiment 1 | | |
| G418 | 35 | 17 |
| G418, FIAU | 23 | 17 |
| Experiment 2 | 19 | 9 |
| G418 | | |

Targeting by Direct Injection of DNA Vectors into Mouse Zygotes

Figure 2B:
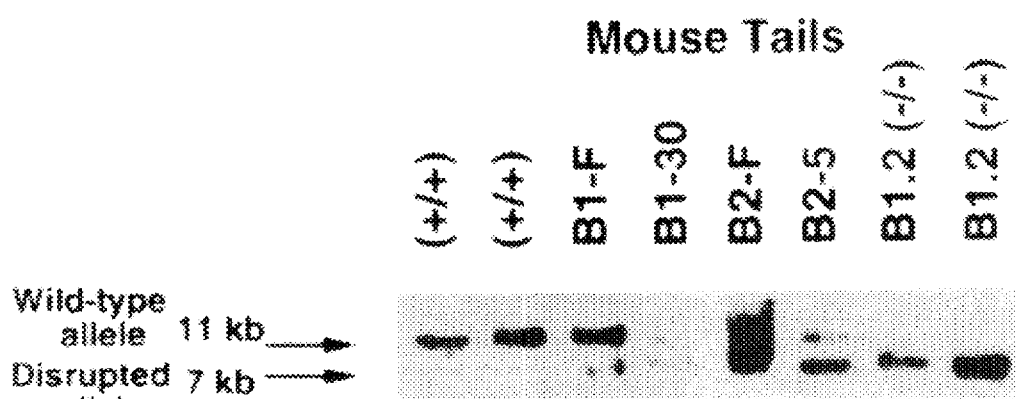

A previous study demonstrated that homologous recombination can occur following microinjection of DNA into mouse zygotes (Brinster et al., Proc. Natl. Acad. Sci. 86:7087–7091, 1989). However, this approach appeared to be inefficient since gene targeting occurred in only 1 of 506 transgenic mice. Encouraged by the high targeting frequency observed in ES cells in the present study, a modified vector ($\beta_3$-KO, FIG. 1) was then microinjected into the pronucleus of mouse zygotes to determine whether homologous recombination at the $\beta_3$-AR locus might occur in the one cell embryo. Initially, injections were performed using inbred 129/SvJ mouse zygotes since these would be isogenic with the targeting vector (derived from a 129/SvJ mouse genomic library). However, the poor breeding performance of 129/SvJ mice severely limited these efforts. To circumvent this problem, hybrid zygotes were used (129/SvJ males mated with FVB/N females), and the targeting vector was injected into the peripheral, presumably male (129/SvJ), pronucleus. The targeting vector was also injected into inbred FBV/N zygotes. As shown in FIG. 2B, two transgenic lines with targeted disruption of the endogenous $\beta_3$-AR were generated (B1 and B2). Further analysis revealed that the B1 founder was mosaic for the targeting event, transmitting the disrupted allele to only two of thirty offspring, and that the B2 founder had a second integration event that was random (as shown below). Founder B2 transmitted the disrupted allele to seventeen of thirty-five offspring, but also transmitted DNA encoding the neomycin-resistant cassette to five of eleven offspring that were wild type at the $\beta_3$-AR locus. Thus, the B2 founder had a second, unlinked, random integration event. Offspring of B2 which were heterozygous at the $\beta_3$-AR locus and lacked any unlinked, random integration event as determined by breeding studies and Southern blot analyses, were further expanded and analyzed. An initial cross of two heterozygous mice resulted in the following eight offspring: two wild type mice, four heterozygous mice, and two homozygous "knockout" mice (the latter two knockout samples are shown in FIG. 2B as B1.2 (−/−)).

Shown in Table II (below) is a summary of all mouse zygote injections. Genomic DNA samples from all live born mice were analyzed by Southern blotting. Transgenic mice were identified with a probe corresponding to the NEO coding sequence. Knockouts were identified using the schemes outlined in FIG. 1. Using the $\beta_3$-KO vector, 513 zygotes were injected and transferred into foster mothers resulting in 158 live born mice of which 23 were found to be transgenic. Of these twenty-three transgenic mice, two had targeted disruption of the $\beta_3$-AR gene (B1 and B2). These two targeting events occurred in the FVB/N transgenic mice that were not isogenic with the targeting vector (129/SvJ).

TABLE II

|  | Zygotes injected | Live born mice | Transgenic mice | Knockout mice |
|---|---|---|---|---|
| FVB/N zygotes | 224 | 65 | 9 | 2 |
| FVB/N × 129 SvJ Hybrid zygotes | 211 | 57 | 10 | 0 |
| 129/SvJ zygotes | 41 | 15 | 1 | 0 |
| Zygotes of uncertain background[a] | 37 | 21 | 3 | 0 |
| Total | 513 | 158 | 23 | 2 |

[a]Two recipient foster mothers gave birth in the same cage, one had received FVB/N zygotes, and the other had received FVB/N × 129/SvJ hybrid zygotes.

$\beta_3$-AR mRNA Levels by RNase Protection Assay

Figure 3:
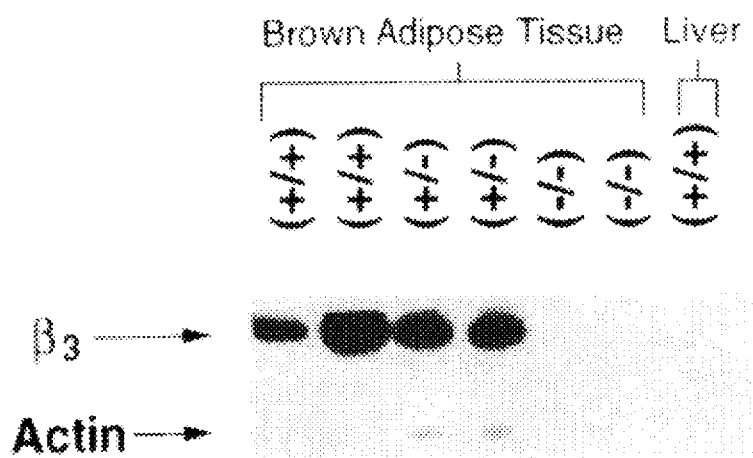

To determine whether $\beta_3$-AR knockout mice lack intact $\beta_3$-AR mRNA, an RNase protection assay was performed on RNA obtained from brown adipose tissue. The probe used in the protection assay corresponded to the 306-bp segment of $\beta_3$-AR coding sequence deleted during the construction of the targeting vector (FIG. 1). As is shown in FIG. 3, a protected $\beta_3$-AR signal was present in wild type and heterozygous mice, but was absent in knockout mice. No signal was observed in liver RNA obtained from wild type mice, a tissue known not to express the $\beta_3$-AR gene. A control signal for actin was observed in all lanes. Thus, $\beta_3$-AR knockout mice were found not to express detectable amounts of $\beta_3$-AR mRNA.

Figure 4:
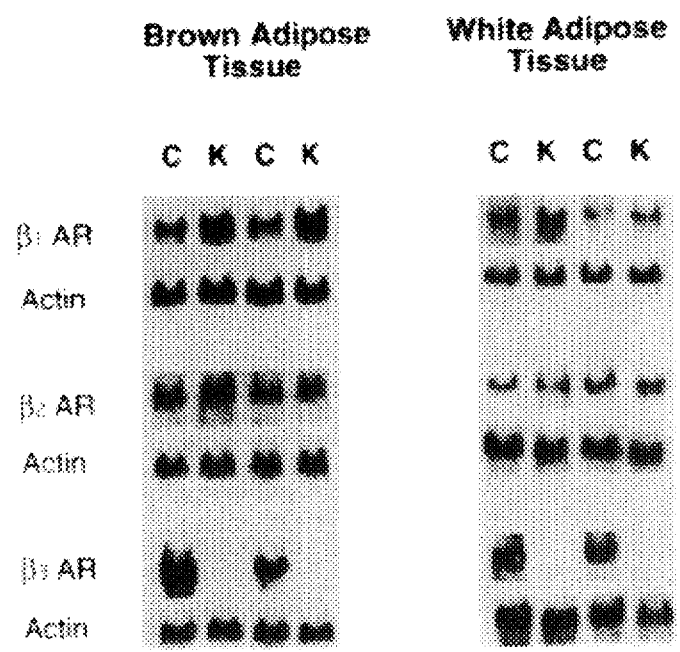

$\beta_1$-, $\beta_2$-, and $\beta_3$-AR mRNA Levels in White and Brown Adipose Tissue by Northern Blotting To determine whether $\beta_1$ and/or $\beta_2$-AR mRNA levels up-regulated in adipose tissue of mice lacking $\beta_3$-ARs, Northern blotting was performed using total RNA isolated from epididymal white adipose tissue and interscapular brown adipose tissue of control and $\beta_3$-AR-deficient male mice. As is shown in FIG. 4, intact $\beta_3$-AR mRNA was not detected in white or brown adipose tissue of knockout mice. Given that no signal was detected using the same $\beta_3$-AR probe in a sensitive RNase protection assay (FIG. 3), it was concluded that the extremely faint signal observed in knockout samples by Northern blotting (FIG. 4) represents non-specific background. $\beta_2$-AR mRNA levels were also found to be unchanged in white and brown adipose tissue of knockout animals (FIG. 4), indicating that compensatory increases in this family member do not occur in $\beta_3$-AR-deficient mice. In contrast, $\beta_1$-AR mRNA levels significantly up-regulated in brown adipose tissue of knockout mice, with a smaller increase observed in white adipose tissue (FIG. 4). PhosphorImager analysis (Molecular Dynamics, Image Quant software) of Northern blots containing white and brown adipose tissue RNA derived from five control and five knockout mice indicated that $\beta_1$-AR mRNA levels were increased by seventy-six percent in brown adipose tissue (p<0.01) and by forty-two percent in white adipose tissue (p<0.05) of $\beta_3$-AR-deficient mice.

Phenotype of $\beta_3$-AR-Deficient Mice

In total, 166 offspring of heterozygous male and female mice were analyzed for genotype at the age of twenty-one days, and the following distribution was observed: +/+, n=45; +/−, n=80; and −/−, n=41. These results closely approximated the expected ratio of 1:2:1, indicating that $\beta_3$-AR deficiency does not adversely affect pre- or postnatal viability.

Data shown in Table III (below) summarize the body weight, fat pad weight, and total body fat content of control and $\beta_3$-AR-deficient mice. These data indicated that there is a tendency for $\beta_3$-AR-deficient mice to have greater lipid stores. In addition, female $\beta_3$-AR-deficient mice appear to have greater lipid stores than males. In experiment 1, the body weights of female were increased by nineteen percent (p<0.05). Male knockout mice in experiment 1 were unaffected. In experiment 2, the mean body weights of knockout animals did not differ statistically based on sex. In males, total body fat stores were increased by thirty-four percent (p<0.05), although epididymal fat pad weights were not significantly greater. In females, fat stores were increased, with total body fat stores of knockout females being 131% greater than controls (p<0.01) and parametrial fat pads from knockout animals weighing 99% more than controls (p<0.05). Blood glucose, serum insulin, and FFA (free fatty acids) levels, all assessed in the fed state, as well as FFA levels following a two-day fast, were normal in knockout animals. Food intake was assessed in experiment 1, and was found to be unchanged in $\beta_3$-AR-deficient mice.

TABLE III

|  | Male | | Female | |
|---|---|---|---|---|
| Parameter | +/+ | −/− | +/+ | −/− |
| Experiment 1 (age 12 weeks) Body weight (g) | 30.9 ± 1.9 | 29.2 ± 1.8 | 18.0 ± 0.9 | 21.5 ± 1.1[a] |
| n | 4 | 4 | 4 | 4 |
| Experiment 2 (age 15 weeks) Body weight (g) | 30.7 ± 1.4 | 31.8 ± 0.8 | 23.0 ± 0.5 | 24.1 ± 0.8 |
| Genital fat pad weight (mg) | 809 ± 135 | 901 ± 76 | 227 ± 62 | 451 ± 86[a] |
| Total body fat (g) | 5.45 ± 0.70 | 7.31 ± 0.48[a] | 1.79 ± 0.32 | 4.14 ± 0.41[b] |
| n | 8 | 8 | 8 | 6 |

[a]p < 0.05 versus +/+ mice.
[b]p < 0.01 versus +/+ mice.

Next, the effects of chronic cold exposure on brown adipose tissue (BAT) of control and $\beta_3$-AR-deficient mice was examined. Cold exposure-induced hypertrophy of brown adipose tissue is a well documented phenomenon which is thought to be mediated by norepinephrine released from sympathetic nerve terminals. When control (+/+) mice were cold-exposed for three weeks, brown fat weight increased by 78%, brown fat protein content by 142%, brown fat DNA content by 66%, and UCP content by 320%. The results (expressed as the mean ±S.E.) of these studies are shown in Table IV (below). Each of these cold exposure-induced responses occurred normally in $\beta_3$-AR-deficient animals. In addition, colonic temperatures in control and knockout mice were normal (37° C.) throughout the three-week study period. Thus, $\beta_3$-ARs are not required for cold exposure-induced hypertrophy of brown adipose tissues.

TABLE IV

| Parameter | -/+ | | -/- | |
|---|---|---|---|---|
| | 23° C. | 4° C. | 23° C. | 4° C. |
| BAT weight (mg) | 149 ± 19 | 265 ± 19[a] | 117 ± 13 | 224 ± 11[a] |
| BAT protein content (mg) | 8.06 ± 0.59 | 19.53 ± 1.79[a] | 7.91 ± 0.99 | 18.63 ± 1.1[a] |
| BAT DNA content (μg) | 136 ± 8 | 226 ± 17[a] | 121 ± 12 | 212 ± 11[a] |
| BAT UCP content (μg) | 446 ± 75 | 1876 ± 281[a] | 479 ± 30 | 2094 ± 183[a] |
| n | 3 | 5 | 3 | 6 |

[a] $p < 0.05$ versus 23° C. animals of the same genotype.

Adenylate Cyclase Activity and Lipolysis

To determine the functional consequences of $\beta_3$-AR deficiency on β-adrenergic signalling, the effects of β-adrenergic agonists on adenylate cyclase activity and lipolysis were assessed. For determination of adenylate cyclase activity (FIG. 5), plasma membranes were obtained from isolated white adipocytes or interscapular brown adipose tissue, and then were incubated in the presence of various agonists. Adenylate cyclase activity was assessed by quantitating the production of cAMP (Salomon, Adv. Cyclic Nucleotide Res. 10:35–55, 1979). To assess lipolysis (FIGS. 6A and 6B), white adipocytes were isolated from epididymal fat pads, and then incubated in the presence of various agonists. Rates of lipolysis were determined by quantitating the release of glycerol.

Figure 5A:
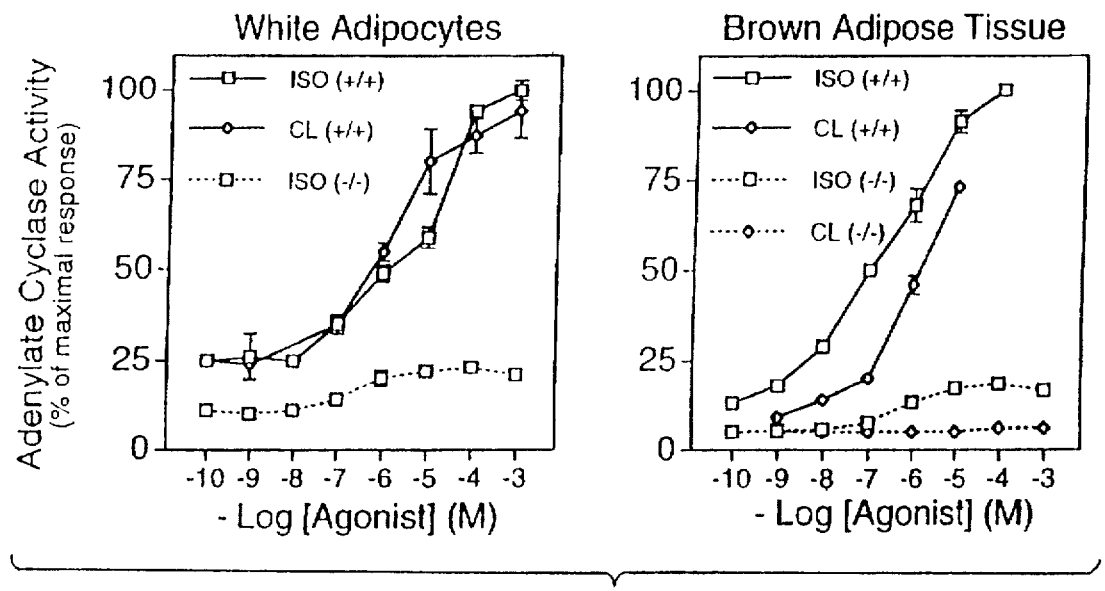
FIG. 5A are graphs showing the dose-response curves for stimulation by isoproterenol (ISO, a nonselective $\beta$-AR agonist) and CL 316,243 (CL, a $\beta_3$-AR selective agonist). Results are expressed as percentage of maximal stimulation by isoproterenol in lean membranes, and are the mean (±S.E.) of three replicates.
Figure 5B:
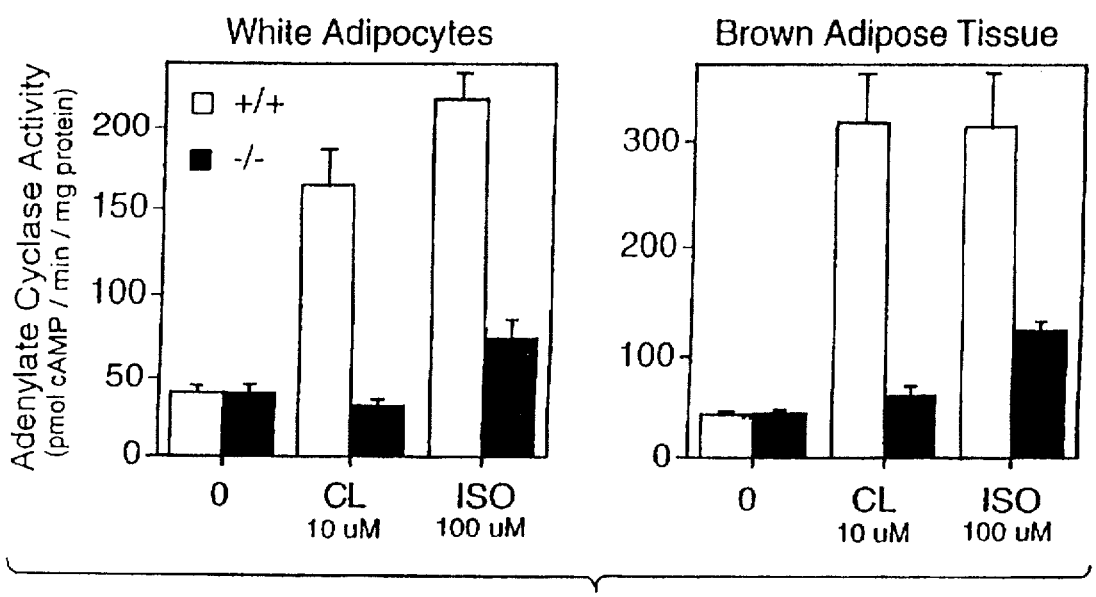
FIG. 5B are graphs showing the adenylate cyclase response to maximally, or near maximally effective doses of CL 316,243 and isoproterenol. Results are expressed as the mean (±S.E.) of ten experiments.

Maximally effective doses of CL 316,243, a $\beta_3$-selective agonist (Bloom et al., J. Med. Chem. 35:3081–3084, 1992), stimulated adenylate cyclase activity in membranes (FIG. 5) and lipolysis in adipocytes (FIGS. 6A and 6B) of wild-type mice. These responses were absent in membranes and cells derived from $\beta_3$-AR-deficient mice (FIGS. 5 and 6). Qualitatively similar results were obtained with submaximal doses of CL 316,243. These results demonstrated that $\beta_3$-AR-deficient mice lacked functional $\beta_3$-ARs, and confirmed that the stimulatory effect of CL 316,243 on these processes is mediated by $\beta_3$-ARs.

Effective doses of isoproterenol, a nonselective β-AR agonist, was observed to stimulate adenylate cyclase activity in membranes derived from wild type mice (FIG. 5). In membranes obtained from $\beta_3$-AR-deficient mice, however, the stimulatory effect of isoproterenol on adenylate cyclase activity was observed to be reduced (by seventy percent in membranes derived from brown adipose tissue and by eighty percent in membranes derived from isolated white adipocytes). Qualitatively similar results were obtained with submaximal doses of isoproterenol. Thus, $\beta_3$-ARs appeared to be responsible for mediating seventy-eighty percent of isoproterenol-induced maximally stimulated adenylate cyclase activity. It is likely that $\beta_1$- and $\beta_2$-ARs mediate the remaining twenty-thirty percent.

Assessment of isoproterenol-stimulated lipolysis in control versus $\beta_3$-AR-deficient adipocytes revealed additional complexity, which involved an interaction between $A_1$ adenosine receptors and the relative roles of $\beta_3$ versus $\beta_1$- and $\beta_2$-ARs. Adenosine induces an inhibitory effect on adenylate cyclase, mediated by $A_1$ adenosine receptors and $G\alpha_i$. It has been recognized previously that significant but variable amounts of adenosine are generated during the isolation and incubation of adipocytes, and that this can have a confounding influence on lipolysis assays (Fain, Mol. Pharmacol. 9:595–604, 1973; Schwabe et al., Arch. Exp. Pathol. Pharmacol. 276:133–148, 1973; Honnor et al., J. Biol. Chem. 260:15122–15129, 1985). To circumvent this problem, it has become common practice to remove endogenously generated adenosine through the addition of adenosine deaminase, and to add a stable $A_1$ adenosine receptor agonist (usually PIA). This procedure effectively clamps the influence of adenosine at a fixed level. In the present study, lipolysis assays were initially performed in the presence of adenosine deaminase and PIA (+ADA, +PIA in FIG. 6). As is shown in FIG. 6A, a maximally effective concentration of isoproterenol was found to stimulate lipolysis in wild type adipocytes by about five-fold. This response was absent in $\beta_3$-AR-deficient adipocytes. The absence of isoproterenol-stimulated lipolysis in $\beta_3$-AR-deficient adipocytes was again observed in a latter series of experiments performed under identical conditions (+ADA, +PIA in FIG. 6B, left panel). In contrast, when the adenosine agonist was omitted from the assay (+ADA, –PIA in FIG. 6B, right panel) isoproterenol-stimulated lipolysis in $\beta_3$-AR-deficient adipocytes was reduced by about thirty-three percent. Isoproterenol-stimulated lipolysis in control adipocytes was only minimally inhibited by PIA (FIG. 6B, left panel versus right panel). Thus, when PIA was present during the assay, $\beta_3$-ARs were responsible for mediating isoproterenol-stimulated lipolysis. When PIA was absent and endogenous adenosine was removed, $\beta_1$- and/or $\beta_2$-ARs appeared to mediate the majority of isoproterenol-stimulated lipolysis.

Adrenocorticotropic hormone (ACTH), which also stimulates lipolysis via a seven-transmembrane receptor $G\alpha_s$-adenylate cyclase-coupled mechanism (Birnbaumer et al., J. Biol. Chem. 244:3468–3476, 1969; Mountjoy et al., Science 257:1248–1251, 1992), was found to increase lipolysis in adipocytes derived from wild type and $\beta_3$-AR-deficient mice (FIG. 6A). Similarly, forskolin, a direct activator of adenylate cyclase, was found to stimulate lipolysis in wild type and $\beta_3$-AR-deficient cells (FIG. 6A). Normal responsiveness to ACTH and forskolin makes it unlikely that impaired responsiveness of $\beta_3$-AR-deficient cells to isoproterenol resulted from a direct inhibitory effect of $\beta_3$-AR deficiency on $G\alpha_s$, adenylate cyclase, or more distal components of the activation pathway for lipolysis.

In Vivo Effects of Adrenergic Agonists on Lipolysis and Thermogenesis

To determine the effect of $\beta_3$-AR deficiency on β-adrenergic signaling in vivo, various adrenergic agonists were administered to control and knockout mice, and the effects on serum levels of FFAs, glycerol, and thermogenesis were assessed. The results (expressed as the mean ±S.E.) of these studies showing the levels of serum free fatty acids and glycerol fifteen minutes after injection of isoproterenol (ISO) and CL 316,243 in control and $\beta_3$-AR-deficient mice are shown in Table V (below). Treatment of control mice with the $\beta_3$-selective agonist, CL 316,243, produced a 3.2-fold increase in serum FFA levels (Table V, below), and a 2-fold increase in oxygen consumption (FIG. 7). Both of these effects were totally absent in $\beta_3$-AR-deficient mice, indicating that they are mediated by $\beta_3$-ARs. When control mice were treated acutely with maximally effective doses of isoproterenol, serum FFA and glycerol levels also increased by two- to three-fold. In contrast to the findings with CL 316,243, these responses to isoproterenol were normal in $\beta_3$-AR-deficient male mice, and only slightly reduced in $\beta_3$-AR-deficient female mice (Table V). Similarly, isoproterenol- and norepinephrine-stimulated oxygen consumption was not significantly reduced in $\beta_3$-AR-deficient male mice (FIG. 7). Together, these findings demonstrated that under normal conditions, $\beta_3$-ARs are not required for the stimulation of lipolysis or thermogenesis by exogenously administered isoproterenol or norepinephrine.

TABLE V

| Parameter | Male | | Female | |
|---|---|---|---|---|
| and drug | +/+ | −/− | +/+ | −/− |
| FFA (μM) Saline | 610 ± 90 | 550 ± 50 | 710 ± 40 | 530 ± 50 |
| CL 316,243 | | | 2,260 ± 350[a] | 630 ± 140[b] |
| ISO | 1.680 ± 127[a] | 1.510 ± 20[a] | 1.630 ± 150[a] | 1.190 ± 100[a,c] |
| Glycerol (μM) Saline | 80 ± 10 | 75 ± 9 | 108 ± 9 | 94 ± 7 |
| ISO | 243 ± 27[a] | 239 ± 15[a] | 218 ± 10[a] | 147 ± 19[a,c] |
| n | 4 | 5 | 4 | 6 |

[a] $p < 0.01$ versus mice of similar genotype treated with saline.
[b] $p < 0.01$ versus +/+ mice treated with CL 316,243.
[c] $p < 0.01$ versus +/+ mice treated with isoproterenol.

Acute Effects of a $\beta_3$-Selective Agonist on Insulin Release and Food Intake Acute treatment with $\beta_3$-selective agonists in vivo has been shown to produce an increase in circulating insulin levels (Yoshida, Am. J. Clin. Nutr. 55:237S–241S, 1992) and a decrease in food intake (Tsujii and Bray, Brain Res. 287:226–232, 1992; Himms-Hagen et al., Am. J. Physiol. 266:R1371–R1382, 1994). To assess the role of $\beta_3$-ARs in mediating these responses, the $\beta_3$-selective agonist CL 316, 243 was administered to control and $\beta_3$-AR-deficient knockout mice, and the effects on insulin concentrations and food intake were determined. Acute treatment with CL 316,243 produced at 140-fold increase in plasma insulin levels, and a fifty-six percent reduction in blood glucose in control mice, but was completely without effect in $\beta_3$-AR-deficient mice (FIG. 8). Similarly, acute treatment with CL 316,243 produced a forty-five percent reduction in food intake in control mice, but was completely ineffective in $\beta_3$-AR-deficient mice (FIG. 9). These results demonstrated that the large effects of acute CL 316,243 treatment on insulin secretion and food intake are mediated by $\beta_3$-ARs.

In sum, the above described experiments have demonstrated that mice with targeted disruption of the $\beta_3$-AR have a modest increase in body fat, indicating that $\beta_3$-ARs play a role in regulating energy balance. $\beta_1$, but not $\beta_2$-AR mRNA levels up-regulate in white and brown adipose tissue of $\beta_3$-AR-deficient mice, indicating that $\beta_3$-ARs mediate physiologically relevant signalling. The ability of CL 316, 243, a selective $\beta_3$-agonist, to increase adipocyte adenylate cyclase activity and lipolysis, serum insulin levels, and whole body energy expenditure, and to reduce food intake is mediated by $\beta_3$-AR.

Reconstituting $\beta_3$-AR Activity in $\beta_3$-AR Deficient mice Using a Human $\beta_3$-AR Gene To express human $\beta_3$-AR in brown fat, $\beta_3$-AR deficient (−/−)transgenic mice have been reconstituted with an 80 kb $\beta_3$-AR human genomic clone as follows. Polymerase chain reaction (PCR) primers (sense: 5'AGAGGAGATACTG-GCTGAGC 3' (SEQ ID NO:1); anti-sense: 5' TGGACT-CAGCATAGCACTCC 3' (SEQ ID NO:2)) designed to amplify a human $\beta_3$-AR sequence (Van Spronsen et al. Eur. J. Biochem. 213:1117–1124, 1993; Emorine et al., Science 245:1118–1121, 1989) were used to screen an arrayed human genomic DNA library constructed in the bacteriophage P1 according to standard techniques (Shepherd et al., 1994; Genome Systems, Inc.). This screen resulted in the isolation of two genomic clones, designated DuPont Merck Pharmaceutical Company Human Foreskin Fibroblast P1 Library (DMPC-HFF) 1-193HA and 1-1163F1. Portions of each clone have been sequenced, and these analyses have demonstrated that both clones contain the human $\beta_3$-AR gene. FIG. 10 shows a schematic illustration of the genomic map for one these clones, DMPC-HFF 1-1163F1.

Generation of Human-$\beta_3$-Adrenergic Mice

Using standard techniques (Hogan et al., 1986), modified for handling large P1 DNA fragments (Linton et al., 1993), the human $\beta_3$-AR genomic insert was injected into the pronucleus of zygotes. Prior to pronuclear injection, the genomic insert was linearized using NotI. The zygotes were generated by mating male and female $\beta_3$-AR deficient homozygous mice (as described herein). Founders were screened using standard PCR methodology according to standard methods (e.g., PCR Technology, H. A. Erlich, ed., Stockton Press, London, 1989; PCR Protocols: A Guide to Methods and Applications, M. A. Innis, D. H. Gelfand, J. J. Sninsky, and T. J. White, eds., Academic Press, Inc., New York, 1990; and Ausubel et al., Current Protocols in Molecular Biology, John Wiley & Sons, 1989). Transgenic lines expressing the human $\beta_3$-AR were expanded and characterized according to conventional methods.

Expression of Human $\beta_3$-AR mRNA in $\beta_3$-AR-Deficient Mice

To determine the tissue-specific expression of human $\beta_3$-AR in the $\beta_3$-AR-deficient background, RNase protection assays were performed according to conventional methods using total RNA isolated from several tissues, including brown adipose tissue, white adipose tissue, liver, stomach, small intestine, skeletal muscle of mice containing the human $\beta_3$-AR gene on the $\beta_3$-AR-deficient background. As is shown in FIG. 11, human $\beta_3$-AR mRNA was detected in brown adipose tissue. No $\beta_3$-AR mRNA was detected in any of the other tissues examined.

Effect of CGP-12177 on $O_2$ Consumption

CGP-12177, a $\beta_1$-AR and $\beta_2$-AR antagonist with partial $\beta_3$-AR agonist activity, was administered to $\beta_3$-AR-deficient knockout mice and knockout mice expressing the reconstituted human $\beta_3$-AR. The effects on oxygen consumption were then assessed according to standard methods (e.g., those described herein). The results of this study (FIG. 12) showed that fifteen minutes after injection of CGP-12177, $\beta_3$-AR-deficient mice had decreased oxygen consumption. In contrast, treatment of knockout mice expressing the reconstituted human $\beta_3$-AR with CGP-12177 produced a twenty percent increase in oxygen consumption. Together, these findings demonstrated that human $\beta_3$-AR activity was reconstituted in transgenic mice containing the human $\beta_3$-AR gene.

The experiments described above were carried out using the following conventional techniques.

Targeting Constructs

Using a mouse 129/SvJ genomic library (Stratagene) and published mouse $\beta_3$-AR sequence (Nahmias et al., *EMBO J.* 10:3721–3727, 1991), $\beta_3$-AR genomic clones were obtained and mapped (FIG. 1). Two targeting constructs were generated: $\beta_3$-KO+TK (for ES cell studies) and $\beta_3$-KO (for zygote microinjections) (FIG. 1). To construct the vectors, the 5' side of the targeting vector (from BamHI to XhoI) was directionally subcloned into PGEM-11 (Promega) to generate p5'$\beta_3$-AR. A segment of $\beta_3$-AR coding sequence was removed by replacing the 306-bp $\beta_3$-AR NheI and XhoI fragment (corresponding to $\beta_3$-AR residue 120, in the middle of the third transmembrane domain, to residue 222, at the COOH-terminal end of the fifth transmembrane domain) with a PGK-NEO-Poly(A) expression cassette, excised from pPGK-NEO-BKS (described below) with XbaI and SalI, to create p5' $\beta_3$-AR+NEO. The right side of the targeting vector (from XholI to SalI) was subcloned into PGEM-11 at the XholI and SalI sites to create p3' $\beta_3$-AR (p3' $\beta_3$-AR clones with intact XhoI and SalI sites were selected). The insert was excised from p5' $\beta_3$-AR+NEO with NotI and SalI, and subcloned into p3' $\beta_3$-AR opened at NotI and XhoI to create the mouse zygote targeting plasmid p$\beta_3$-KO sites. To generate the ES cell targeting plasmid (p$\beta_3$-KO+TK), the entire insert was excised from p$\beta_3$-KO with NotI and SalI and subcloned into pHSV-TK-PGEM (described below) opened at NotI and XhoI. pPGK-NEO-BKS was prepared by subcloning the PGK-NEO-Poly(A) expression cassette (Adra et al., *Gene* 60:65–74, 1987) into bluescript KS at the EcoRI and HindIII sites. pHSV-TK-PGEM was prepared by subcloning the HSV-TK expression cassette pIC19R/MC1-TK (Mansour et al., *Nature* 336:348–352, 1988) excised with XhoI and SalI into PGEM-11 at XhoI and SalI (clones with intact XhoI and SalI sites were selected).

ES Cell Culture

J1-ES cells, derived from a 129/terSv embryo, were cultured on γ-irradiated neomycin-resistant primary embryo fibroblasts as described by Li et al. (*Cell* 69:915–926, 1992). Fifteen million ES cells were electroporated with twenty micrograms of p$\beta_3$-KO+TK (linearized with NotI), and plated on ten ten-centimeter plates. On the following day, five plates received G418 (182 μg/ml active dose), and the other five plates received G418 and FIAU (0.2 μM 1-[2-deoxy, 2-fluoro-β-D-arabinofuranosyl]-5-iodouracil; Bristol Meyers). Following eight days of selection, drug-resistant clones were expanded individually, and genomic DNA was obtained for Southern blot analysis (FIGS. 1 and 2).

Zygote DNA Microinjections

Prior to injection, the $\beta_3$-KO targeting vector was excised from p$\beta_3$-KO using NotI and SalI and then separated from the plasmid sequence using gel purification. Approximately 300–500 copies of the 14-kb $\beta_3$-KO insert were injected into the male pronucleus of zygotes using standard techniques (e.g., Hogan et al., *Manipulating the Mouse Embryo*, Cold Spring Harbor Laboratory, Cold Spring Harbor, N.Y., 1996). Zygotes for injection were generated by mating 129/SvJ females and males (129/SvJ zygotes), FVB/N females and 129/SvJ males (FVB/N [mult] 129/SvJ hybrid zygotes), or FVB/N females and males (FVB/N zygotes). Injected zygotes were transferred to FVB/N pseudopregnant recipients as described by Hogan et al. (supra), and genomic DNA was obtained from live born offspring for Southern blot analysis (FIG. 2). All animals had free access to food (Purina Chow 5008) and water, and were handled in accordance with the principles and guidelines established by the National Institutes of Health.

DNA and RNA Analysis

Genomic DNA was isolated from ES cells and mouse tails by sodium dodecyl sulfate/proteinase K digestion followed by salt precipitation as described by Miller et al. (*Nucleic Acids Res.* 16:1215, 1988). The DNA was analyzed using standard Southern blotting techniques (e.g., Sambrook et al., *Molecular Cloning: A Laboratory Manual*, 2nd ed., Cold Spring Harbor Laboratory, Cold Spring Harbor, N.Y., 1989) or conventional PCR methods. Total RNA was isolated from interscapular brown adipose tissue, epididymal white adipose tissue, and liver using either the guanidium-cesium chloride method (FIG. 3) (Sambrook et al., supra) or RNA-zol (FIG. 4) (Cinna/Biotecx Laboratory, Houston, Tex.). $\beta_1$-, $\beta_2$-, $\beta_3$-AR and actin mRNAs were detected using standard Northern blotting techniques and thirty micrograms of total RNA (Sambrook et al., supra). Murine $\beta_1$-(Cohen et al., *DNA Cell Biol.* 12:537–547, 1993), $\beta_2$-(Allen et al., *EMBO J.* 7:133–138, 1988), $\beta_3$-AR (Nahmias et al., *EMBO J.* 10:3721–3727, 1991) and β-actin (Alonso et al., *J. Mol. Evol.* 23:11–22, 1986) hybridization probes were generated using random priming from cDNA templates corresponding to codons 88–176 of the $\beta_1$-AR (263 bp), codons 230–386 of the $\beta_2$-AR (465 bp), codons 120–222 of the $\beta_3$-AR (306 bp), and codons 220–303 of β-actin (250 bp). The 306-bp probe used to detect $\beta_3$-AR mRNA levels represents the same NheI-XhoI $\beta_3$-AR fragment detected during the construction of the targeting vector (FIG. 1). $\beta_3$-AR and β-actin mRNAs were also detected using an RNase protection assay (Jakubowski and Roberts, *J. Neuroendocrinol.* 4:79–89, 1992). Radioactive $\beta_3$-AR and actin cRNA probes were transcribed from the fragments described above. RNA samples (twenty micrograms of total RNA) were hybridized with both $^{32}$P-labeled cRNA probes (0.5 ng) at 30° C. The protected probes were resolved on a nondenaturing 5% acrylamide gel. The gels were dried and exposed to autoradiographic film.

Body Weight, Perigenital Fat Pad Weights, and Total Body Lipid Analyses

Studies were performed on animals that had free access to water and chow (Purina 5008), and that were maintained at 23° C. All mice were of the following genotype: +/+ or –/– at the $\beta_3$-AR gene locus on an inbred FBV background. Two separate experiments were performed and the results are shown in Table II. In experiment 1, male and female control (+/+) and knockout (–/–) littermates of heterozygous parents were weaned at age twenty-one days, and housed individually. Body weights were obtained at the age of twelve weeks. In experiment 2, control (+/+) offspring derived from wild type parents and knockout (–/–) offspring derived from knockout parents were weaned at age twenty-one days. Only offspring from litters containing nine to eleven mice were used; all others were excluded. The males were housed individually, and females of similar genotype were housed two per cage. Body weight, perigenital fat pad weights (male, epididymal fat pads; female, parametrial fat pads), and carcasses were analyzed at the age of fifteen weeks. For each individual animal, the paired fat pads were combined and weighed. Total body lipid content was assessed using alcoholic potassium hydroxide digestion with saponification of all fats, neutralization, and then enzymatic determination of glycerol according to conventional methods (Salmon and Flatt, *Int. J. Obesity* 9:443–449, 1985; Lowell et al., *Nature* 366:740–742, 1993).

Brown Adipose Tissue and Chronic Cold Exposure

Male control (+/+) and knockout (−/−) animals, age ten weeks, were housed individually with free access to water and chow. The animals were divided and maintained at either room temperature (23° C.) or at 4° C. Three weeks later, the interscapular depot of brown fat was obtained and assessed for the following parameters: wet weight, total protein, DNA and uncoupling protein (UCP) content. Protein and UCP were determined as described Lowell et al. (supra), and DNA was quantitated using the Hoechst dye 33258 and a Hoefer fluorometer according to the manufacturer's recommended protocol (Hoefer Scientific Instruments).

Lipolysis and Adenylate Cyclase Assays

Adipocytes were isolated from epididymal fat pads of male mice using collagenase digestion according to standard methods (Rodbell, *J. Biol. Chem.* 239:375–380, 1964; Shepherd et al., *J. Biol. Chem.* 268:22243–22246, 1993). For analysis of adenylate cyclase activity, membranes were obtained from either isolated white adipocytes (Greenberg et al., *J. Biol. Chem.* 262: 4564–4568, 1987) or interscapular brown adipose tissue (Chaudhry and Granneman, *Am. J. Physiol.* 261:R403–R411, 1991). Isolated membranes were assayed for adenylate cyclase activity in the presence of varying concentrations of agonists over a thirty minute period according to Salomon (*Adv. Cyclic Nucleotide Res.* 10:35–55, 1979), modified by the addition of tritiated cAMP to correct for cAMP recovery.

For analysis of lipolysis, isolated white adipocytes (100 μl of a 10% isolate fat cell suspension) were incubated in a final volume of 500 μl, and glycerol release was measured over a fifteen minute period. Previous studies have demonstrated that glycerol release is linear for at least fifteen minutes of incubation. Except where noted, the incubation medium consisted of a Krebs-Ringer-Hepes (30 mM) buffer (pH 7.4) supplemented with 2.5% bovine serum albumin (fraction V), 10 μM PIA ($N^6$-[R-(−)-1-methyl-2-phenyl]adenosine), 1 unit/ml adenosine deaminase, and varying concentrations of agonists. Glycerol content of the incubation medium was determined using a sensitive radiometric assay (Bradley and Kaslow, *Anal. Biochem.* 180:11–16, 1989), and fat cell number was assessed as described previously (Hirsh and Gallian, *J. Lipid Res.* 19:269–273, 1978; Cushman and Salans, *J. Lipid Res.* 19:269273, 1978).

In Vivo Effects of β-AR Agonists on Serum Levels of FFAs, Glycerol, Glucose, and Insulin CL 316,243, isoproterenol, or saline were injected intraperitoneally into control and $\beta_3$-AR-deficient mice; fifteen minutes later the animals were quickly sacrificed using a small animal decapitator. Whole blood was collected and analyzed for blood glucose levels (One Touch Blood Glucose Meter, Lifescan, Inc., Milpitas, Calif.). Serum was then isolated and assayed for FFAs (NEFA C kit, Wako Pure Chemical Industries, Ltd.), glycerol (GPO-Trinder Kit, procedure 337, Sigma), and insulin (rat insulin kit, Linco Research Inc., St. Louis, Mo.) according to the manufacturers' protocols.

In Vivo Effects of β-AR Agonists on $O_2$ Consumption

Oxygen consumption was measured as described by Lowell et al. (supra) in twelve-week-old control, $\beta_3$-AR-deficient male mice, and $\beta_3$-AR-deficient knockout mice expressing the human $\beta_3$-AR gene. The animals were conscious for studies using CL 316,243, isoproterenol, and CGP-12177 (Research Biochemicals International, Natick, Mass.), but were anesthetized for studies using norepinephrine.

In Vivo Effects of CL 316,243 on Food Intake

Control and $\beta_3$-AR-deficient male mice, eight weeks old, were treated with an intraperitoneal injection of either saline or CL 316,243 (1 mg/kg) on day 0. To acclimate the mice to injections and handling, saline was injected daily for three days preceding day zero of the study. The mice were housed individually during the study. Food was weighed before injection and twenty-four hours after, and the differences were assumed to represent grams of food eaten per day. The cages were inspected for food spillage, and none was noted.

Reagents and Statistics

All reagents, except where noted, were obtained from Sigma and were of the highest reagent grade. Tritiated cAMP and [$\alpha^{32}$P]ATP were obtained from ICN (Costa Mesa, Calif.). All statistical analyses were performed using the unpaired, two-tailed t test.

Screening Methods

As discussed above, the experimental results described herein have demonstrated that $\beta_3$-AR knockout mice lack functional $\beta_3$-ARs, and that $\beta_3$-AR gene activity is restored in a human tissue-specific manner when $\beta_3$-AR deficient (−/−) transgenic mice are reconstituted using the human $\beta_3$-AR gene. Based on this discovery a screening procedure has been developed for identifying therapeutic compounds that can be used to stimulate $\beta_3$-AR activity, and that are useful as anti-obesity and anti-diabetes agents. In general, the method involves screening any number of compounds for therapeutically-active agents by employing the transgenic animals described herein. Based on our above results, it will be readily understood that a compound that increases human $\beta_3$-adrenegic receptor activity in a transgenic animal (e.g., the mouse described herein) provides an effective therapeutic agent in a mammal (e.g., a human patient). Since the screening procedures of the invention are performed in vivo, it is unlikely that the identified compounds will be highly toxic to a mammalian host organism (e.g., a human patient). In addition, the invention also makes available high-throughput in vitro screening methods for the screening of large quantities of candidate compounds.

Accordingly, the methods, materials, and animals of the invention simplify the evaluation, identification, and development of active agents such as drugs for the treatment of a variety of diseases, including obesity and diabetes. In general, the screening methods of the invention provide a facile means for selecting any number of compounds of interest from a large population which are further evaluated and condensed to a few active and selective materials. Constituents of this pool are then purified and evaluated in the methods of the invention to determine their activity according to conventional methods.

For example, candidate $\beta_3$-AR agonists are assessed for their ability to stimulate adenylate cyclase activity, lipolysis and thermogenesis in brown fat. Methods for these analyses are performed to any conventional protocol, e.g., those methods described above. Administration of the candidate compound is by any known route, e.g., intrapertioneally, and at a range of concentrations. Following an appropriate period of time, the animal is assessed for the effect of the compound compared to control animals. For example, the effects of a candidate $\beta_3$-AR agonist on lipolysis and adenylate cyclase activity is determined using incubated isolated adipocytes and membrane preparations obtained from brown fat of control, $\beta_3$-AR deficient mice, and human $\beta_3$-AR mice. Brown fat plasma membranes are used for determination of adenylate cyclase activity, isolated brown adipocytes for assessment of lipolysis, and intact animals for measurement of thermogenesis ($O_2$ consumption). In addition, as is described above, candidate compounds may also be evaluated for their effects on increased energy expenditure (Lowell et al., supra), decreased food intake (Tsujii and Bray, supra; Himms-Hagen et al., supra), and increased insulin levels (Yoshida, supra; Sennitt et al., *Biochem. Pharmacol.* 34:1279–1285, 1985).

By comparing control mice, $\beta_3$-AR deficient mice, and human-$\beta_3$-mice in their responses in the above treatments the potency of candidate agonists against the human $\beta_3$-AR receptor is determined in vivo and in vitro. Since the therapeutic action of these drugs is mediated via fat tissue (e.g., brown adipose tissue), the above screening procedure provides for the identification of drugs that are efficacious in humans. A useful therapeutic agent is one that promotes, increases, or stimulates human $\beta_3$-AR activity.

Transgenic animals that express human $\beta_3$-AR may be used to obtain animals with additional phenotypes, e.g., phenotypes associated with obesity and diabetes. This is accomplished by combining the different genotypes of different animals by cross-breeding the animals containing the different genotypes, or by integrating an appropriate transgene into a zygote or ES cell of an animal. Transgenic animals expressing human $\beta_3$-AR, but not rodent, may be cross-bred with animals having a predisposition toward obesity or diabetes. For example, genetically obese rodents (ob/ob, db/db, fa/fa, and $A^y$) develop marked obesity. Alternately, mice can be rendered obese by administration of a high-fat diet or by hypothalamic brain lesion (e.g., by using gold-thioglucose as described by Maffei et al., *Proc. Natl. Acad. Sci.* 92:6957–6960, 1995).

Cells from the transgenic animals of the invention are also useful as a source of cells for cell culture, and for the preparation of cell membranes that are useful for analyzing the effects of candidate agonists on human $\beta_3$-AR activity.

For example, to enable mass screening of large quantities of natural products, extracts, or compounds in an efficient and systematic fashion, membranes from brown fat adiopcytes are prepared in wells of a microtiter plate, facilitating the semiautomation of manipulations and full automation of data collection. To evaluate the ability of a test compound or extract to promote or stimulate human $\beta_3$-AR activity, a test compound or extract is inoculated at an appropriate dosage into a microtiter well containing brown adipose tissue membranes that are prepared from wild-type, knockout mice, and knockout mice that are transgenic for the human $\beta_3$-AR gene for an adenylate cyclase assay according to the methods described herein. If desired, various concentrations of the test compound or extract can be inoculated to assess dosage effect on adenylate cyclase assays. Control wells are prepared with a known agonist (e.g., CL 316,243) or in the absence of a test compound or extract. Comparative studies between treated and control wells are used to determine the relative efficacy of the test molecule or compound in promoting adenylate cyclase activity. A test compound that effectively stimulates, boosts, enhances, increases, or promotes adenylate cyclase activity is considered useful in the invention.

Use

The methods and animals of the invention provide a simple means for identifying any number of compounds that are capable of stimulating $\beta_3$-AR activity. Accordingly, a chemical entity discovered to have medicinal value using the methods described herein are useful as a drug, or as information for structural modification of existing $\beta_3$-AR agonist compounds, e.g., by rational drug design.

For therapeutic uses, the compositions or agents identified using the methods disclosed herein may be administered systemically, for example, formulated in a pharmaceutically-acceptable buffer such as physiological saline. Preferable routes of administration include, for example, oral, subcutaneous, intravenous, intraperitoneally, intramuscular, or intradermal injections which provide continuous, sustained levels of the drug in the patient. Treatment of human patients or other animals will be carried out using a therapeutically effective amount of an effect $\beta_3$-AR agonist in a physiologically-acceptable carrier. Suitable carriers and their formulation are described, for example, in Remington's *Pharmaceutical Sciences* by E. W. Martin. The amount of the agonist to be administered varies depending upon the manner of administration, the age and body weight of the patient, and with the type of disease and extensiveness of the disease. Generally, amounts will be in the range of those used for other agents used in the treatment of obesity and diabetes, although in certain instances lower amounts will be needed because of the increased specificity of the compound. For example, for systemic administration a compound is administered typically in the range of 0.1 ng–1 g/kg body weight. Such dosages are administered in a manner free from unwanted side-effects.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A transgenic mouse whose germ cells and somatic cells contain a homozygous disruption of the endogenous $\beta_3$-adrenergic receptor gene, wherein said disruption comprises the insertion of a selectable marker sequence, and wherein said disrupted $\beta_3$-adrenergic receptor gene results in said mouse lacking detectable levels of endogenous $\beta_3$-adrenergic receptor and exhibiting reduced adenylate cyclase activity in membranes of said mouse or reduced lipolysis in adipocytes of said mouse as compared to a wild-type mouse in response to the administration of a $\beta_3$-adrenergic receptor agonist.

2. A transgenic mouse of claim 1, whose germ cells and somatic cells additionally comprise a transgene encoding a human $\beta_3$-adrenergic receptor, wherein said transgene is expressed in brown adipose tissue at levels sufficient for reconstitution of functional human $\beta_3$-adrenergic receptor activity.

3. A method of producing the transgenic mouse of claim 2, said method comprising:

(a) producing and providing a transgenic mouse of claim 1 lacking detectable levels of $\beta_3$-adrenergic receptor and exhibiting reduced adenylate cyclase activity in membranes of said mouse or reduced lipolysis in adipocytes of said mouse as compared to a wild-type mouse in response to the administration of a $\beta_3$-adrenergic receptor agonist;

(b) introducing a human $\beta_3$-adrenergic receptor transgene encoding a functional human $\beta_3$-adrenergic receptor into the pronucleus of a zygote derived from the mouse of claim 1, said zygote containing a homozygous disruption of the endogenous $\beta_3$-adrenergic receptor gene;

(c) transplanting said mouse zygote into a pseudopregnant mouse;

(d) allowing said zygote to develop to term;

(e) obtaining a founder mouse carrying said transgene; and (f) breeding said founder mouse with a wild-type mouse to obtain F1 progeny that express the human $\beta_3$-adrenergic receptor in brown adipose tissue at levels sufficient for reconstitution of functional human $\beta_3$-adrenergic receptor activity.

4. An isolated cell line derived from the transgenic mouse of claim 1 or claim 2.

5. A method of screening for a compound that increases human $\beta_3$-adrenergic receptor activity, said method comprising, exposing the transgenic mouse of claim 2 to said compound, and determining the activity of said human $\beta_3$-adrenergic receptor in said mouse, wherein an increase in said receptor activity as compared to an untreated mouse of claim 2 being indicative of a compound functioning to increase human $\beta_3$-adrenergic receptor activity.

6. The method of claim 5, wherein said method comprises determining oxygen consumption.

7. The method of claim 5, wherein said method comprises determining energy expenditure.

8. The method of claim 5, wherein said method comprises determining food intake.

9. The method of claim 5, wherein said method comprises determining insulin secretion.

10. The method of claim 5, wherein said method comprises determining glycemic control.

11. The method of claim 5, wherein said method comprises determining lipolysis using brown fat adipocytes.

12. The method of claim 5, wherein said method comprises determining adenylate cyclase activity using brown fat adipocytes.

13. A transgenic mouse of claim 1, wherein said mouse is post-natal.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

```
( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:1:

AGAGGAGATA CTGGCTGAGC                                               20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TGGACTCAGC ATAGCACTCC                                               20
```